United States Patent [19]

Boyd et al.

[11] Patent Number: 4,600,016

[45] Date of Patent: Jul. 15, 1986

[54] METHOD AND APPARATUS FOR GAIT RECORDING AND ANALYSIS

[75] Inventors: Timothy L. Boyd, Ringgold, Ga.; Dennis L. Bizzoco, Signal Mountain, Tenn.

[73] Assignee: Biomechanical Engineering Corporation, Chattanooga, Tenn.

[21] Appl. No.: 769,437

[22] Filed: Aug. 26, 1985

[51] Int. Cl.$^4$ .............................................. A61B 5/10
[52] U.S. Cl. .................................... 128/782; 128/779
[58] Field of Search ................. 128/779, 782; 352/53, 352/89, 243; 354/293

[56] References Cited

U.S. PATENT DOCUMENTS

| 3,894,437 | 7/1975 | Hagy et al. | 128/779 |
| 4,515,455 | 5/1985 | Northmore | 354/293 |

Primary Examiner—Kyle L. Howell
Assistant Examiner—Randy Citrin
Attorney, Agent, or Firm—Alan Ruderman

[57] ABSTRACT

A method and apparatus for use in analyzing the gait of a subject has an elongated transparent platform over which the subject may stride and a moveable camera disposed below the platform for viewing the plantar aspects of the subject's foot while the subject strides. The camera is mounted on a trolley driven by a cable and pulley system connected to a belt worn by the subject so that the camera is moved in synchronism with the strides of the subject. High intensity lighting including a fluorescent lamp is placed closely adjacent to one edge of the platform while the remaining edges are covered with highly reflective material to minimize loss of light. The surface of the platform is heated by electrical heating elements so as to preclude the formation of condensation as the subject strides over the platform.

20 Claims, 5 Drawing Figures

METHOD AND APPARATUS FOR GAIT RECORDING AND ANALYSIS

BACKGROUND OF THE INVENTION

This invention relates to a method and apparatus for the analysis and diagnosis of the gait of human beings and more particularly to a method and apparatus for viewing the plantar aspects of the feet while in motion, i.e., the changes in the area of contact as a patient walks for purposes of analyzing and diagnosing the natural full gait cycle of the patient.

A satisfactory system for the biomechanical gait analysis of human beings for the diagnosis and treatment of podiatric and related health problems is not presently available. Such a system may be used to diagnose and predict potential health problems, monitor treatment of existing problems, design prosthesis and orthotic devices and improve the design of footwear. Obviously such a system would provide an additional important tool to that presently available to podiatrists, orthopedists, neurologists and neurosurgeons, pediatricians, physicians specializing in physical rehabilitation and sports medicine, and to physical therapists, orthotists (those who produce specialized footwear), prosthetists (those who produce artificial body parts) among others. The equipment available and the known prior art, however, has not provided the means for studying the patient in motion and obtaining pictures of a foot's plantar aspects while in motion. As one walks the contact and noncontact surface areas of the foot change continuously. Quantifying the amount of contact area, amount of pressure exerted, the relationship of the former to the latter and all in relationship to time as each foot moves from heel strike to toe off positions during the normal gait cycle would produce information not presently available to practitioners in the arts.

One full gait cycle occurs between heel strike of one foot to heel strike by the same foot at the next step. A portion of this cycle for each foot, e.g., approximately 62% is the "stance phase" beginning with heel strike and terminating with toe off during which time the foot bears body weight. The remaining portion of the gait cycle for each foot, e.g., approximately 38% is the "swing phase" between toe off and heel strike and during which the foot is non-weight bearing and swings between steps. "Stance phase" of gait refers to the time intervening from the heel contact of the foot to the end of toe off of the same foot. "Mid stance" refers to the period from heel strike to just before heel off of the same foot. Heel off to toe off refers to the propulsive phase of gait of the single foot. During the mid stance period of one foot the other foot is in the swing phase of its gait cycle so that the weight bearing foot is alone carrying body weight. There is a phase at the end of toe off of one foot and the early heel contact of the contralateral foot when both feet bear weight. The toes bear weight during the propulsive period while they are inactive during the heel strike period and it is uncertain how significant the weight bearing of the toe is during midstance. During the swing phase the foot is carried from one step to the next. If the gait cycle is improper, the contact surface of the foot will not permit the forces acting on the foot during the various periods of the stance phase to be transferred through the various joints correctly, and this results in compensating shifts of various load bearing parts of the body, which over time produces damage to the parts thereof. For example, some spine problems can be traced to an improper gait resulting in abnormally restricted motion at certain joints so that the force of heel strike during the stance phase is not absorbed by the joints within the foot and lower extremity but are transmitted directly into the trunk of the body without proper attenuation of forces. Certain knee problems can also be traced to improper gait. Degenerative joint disease, muscle spasm and chronic low back pain are possible problems associated with faulty shock absorption due to an improper gait.

The relative positions of both feet during the gait cycle is important in determining the stage of the cycle for either foot. Watching a person walk and observing the motion and position of the foot throughout the gait cycle is extremely valuable in clinical examination and treatment.

The prior art, however, has not provided the practitioner with the tools necessary to study in detail the patient while in motion and to make true dynamic gait analysis of the patient's natural gait. In the known prior art, small platforms or the like are provided on which a patient walks or stands, and either a measurement, a print or another image is obtained of the foot at a particular instant of time only. Thus, in many of the prior art apparatus the results provide static measurement, merely measure or analyze one foot at a time without taking into consideration the effect the other foot has on the measured foot, or fails to show the effect on, for example, the heel of the foot when the toe is just coming off etc. Neither does any prior art quantify the length of time in various parts of the gait cycle in standardized normals, baselines or typical pathological patterns. Examples of such prior art are the Walking Program Record marketed by Shutrak ® which provides foot prints on a carbonized sheet of paper (see U.S. Pat. No. 4,183,552) as a patient walks or stands on a hard surface, and the piezoelectric measuring platform marketed by Kistler which provides a static measurement of the force components on one foot along three axes. In Elftman U.S. Pat. No. 2,325,490, a patient walks over a light reflective material on a transparent plate to press the material against the plate for obtaining photographic recordings of the pressure areas. However, the foot per se is not visualized—only the points of pressure contact of the reflecting material and again no time relationships are derived. Moreover, the actual surface area of a foot is not obtained because of the "cone" effect due to the foot contacting the reflecting material. In Hagy et al. U.S. Pat. No. 3,894,437 and Manley et al. U.S. Pat. No. 4,267,728 a subject walks on a small force plate or transparent platform and the forces on one foot at a time of the subject is analyzed. The apparatus in both of these patents results in the subject unnaturally altering his gait so as to step with the one foot onto the platform. Moreover, only the force at a specific instant of time is determined. In Anderson et al. U.S. Pat. No. 4,416,293 a subject strides on a treadmill and the gait is observed by video and audio equipment. Here the upper body is fixed by holding rails of the treadmill so that the natural gait of the subject is again altered and the plantar aspect of the foot is not visualized.

An additional difficulty not addressed by or adequately solved by the prior art when viewing the foot when it is pressed against a hard surface, is the determination of the true beginning and termination of the contact area. Since the bottom of the foot is an uneven pliable compressible heated surface there is a problem with determining surface area contact due to the lack of contrast between the areas of contact and noncontact plus the production of condensation as the foot contacts the surface when viewed through a transparent smooth rigid surface at ambient temperature.

SUMMARY OF THE INVENTION

Consequently, it is a primary object of the present invention to provide a method and apparatus for the biomechanical analysis of humans while in motion by obtaining a record of their natural gait.

It is another object of the present invention to provide a method and apparatus for observing, photographing and obtaining data of the plantar aspects of the feet of humans while in motion during the natural gait of the subject for use in the functional analysis of the foot and its interrelationships to the entire body.

It is a further object of the present invention to provide a method and apparatus for viewing during the natural gait of a person the contact and noncontact areas of the foot and how it changes as the person walks through a number of gait cycles of both feet.

It is a still further object of the present invention to provide a method and apparatus for enabling a practitioner to precisely distinguish the contact area of the foot and determine the force variations while maintaining the integrity of the gait of the subject utilizing an elongated specially lighted and heated platform over which the subject makes a number of strides so as not to alter or deform the natural or normal gait and by viewing the plantar aspects of the foot throughout the gait cycle while the subject strides through at least a number of steps.

Accordingly, the present invention provides a raised platform having a transparent surface over which a subject walks. High intensity lighting is disposed adjacent one edge of the platform while the remaining edges of the platform are covered by highly reflective material so that substantially all the light is retained within the platform. Mounted below the platform is a camera which is driven in synchronism with the movement of the subject as he or she strides across the platform. Condensation caused by contact of the subject's foot against the platform is alleviated by maintaining the surface of the platform at elevated temperatures approaching that of the surface temperature of the feet. Preferably the camera is a video camera and the images therefrom may be recorded and viewed on a monitor and with the aid of computer enhancement and computer simulation, not only can the plantar aspects of the foot be clearly viewed and studied but also the skeleton of the foot can be studied by simulating bone movement within the foot during the gait cycle.

In the specific form of the invention a video camera beneath the platform is mounted on a trolley which follows the subject as he walks along the platform by virtue of a simple trolley drive actuated by a member attached to and moveable with the subject. Specifically, this drive is merely a cable and pulley drive system attached to the trolley and to a belt worn by the subject.

The transparent platform preferably is a plastic material such as acrylic on the surface or within which electric heating strips are disposed for maintaining appropriate temperatures of the platform to eliminate the condensation problem.

The lighting system includes a florescent lamp placed closely adjacent to one edge of the transparent platform and enclosed to ensure that light is concentrated within the platform, and the reflecting material on the other edges of the platform retain the light within the platform and minimize the light rays reflecting off the top and bottom surfaces so that the contact area of the foot on the surface of the platform is highly visible and distinguishable beneath the platform due to the extemely high level of contrast between the contact and noncontact areas.

BRIEF DESCRIPTION OF THE DRAWINGS

The particular features and advantages of the invention as well as other objects will become apparent from the following description taken in connection with the accompanying drawings, in which.

DESCRIPTION OF THE PREFERRED EMBODIMENT

Figure 1:
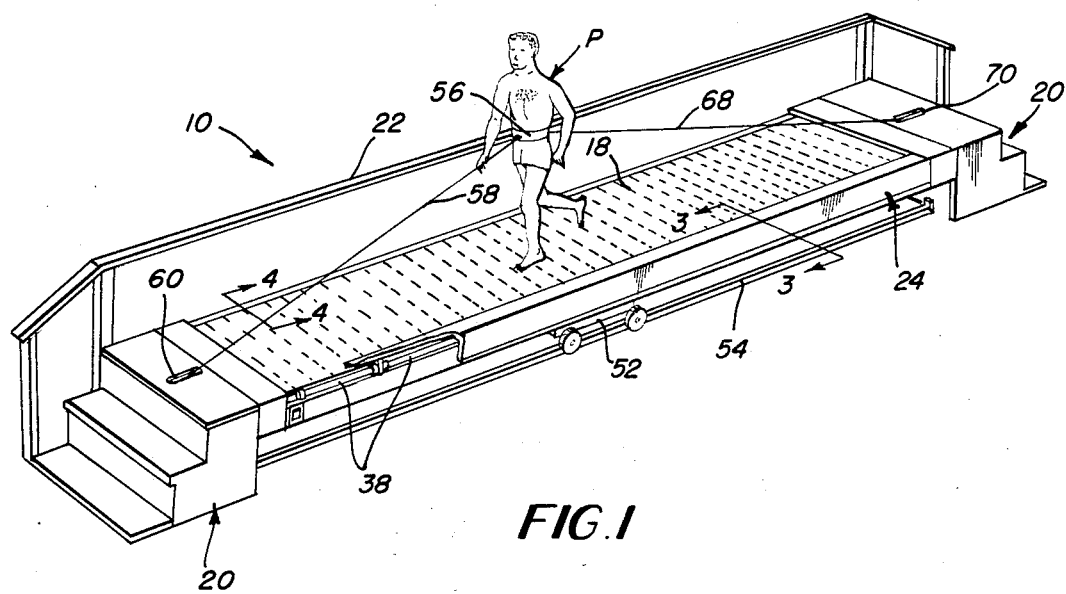
FIG. 1 is a perspective view of apparatus constructed in accordance with the principles of the present invention for analyzing the gait of a subject as the subject strides over a transparent platform.
Figure 2:
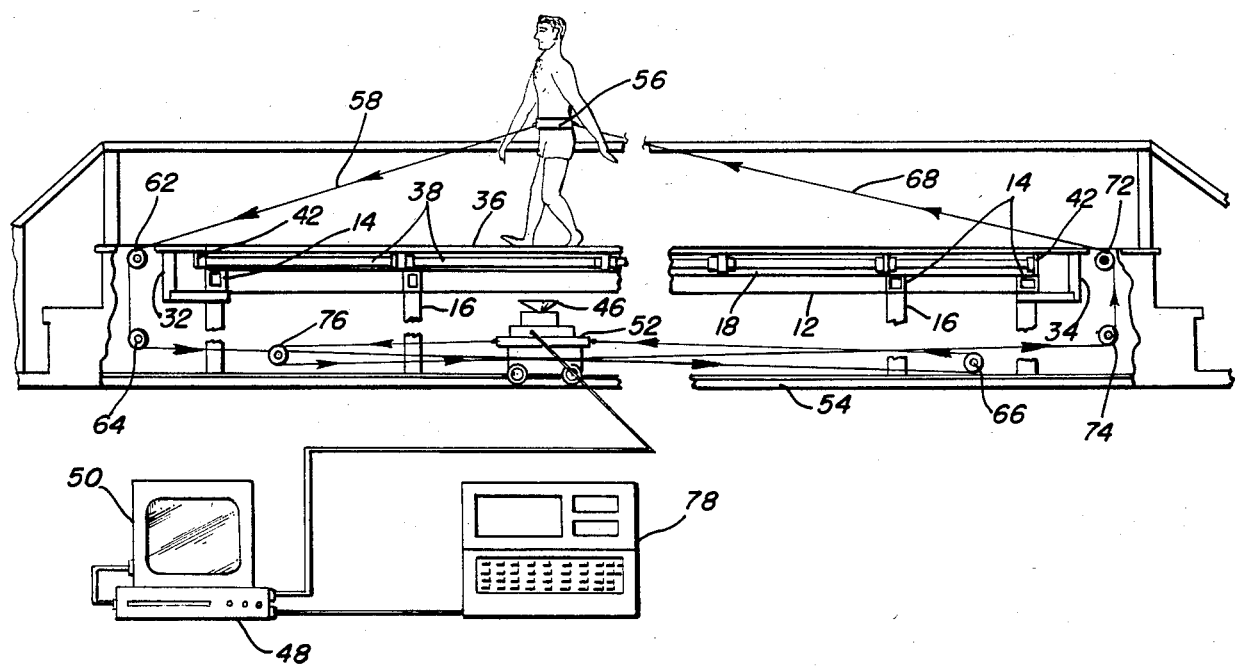
FIG. 2 is a side elevational view of the apparatus illustrated in FIG. 1 with portions thereof broken away and illustrating diagrammatically certain aspects of the invention.

Referring now to the drawings, apparatus constructed in accordance with the principles of the present invention generally comprises a table 10 constructed from a number of structural beam members which may include a number of elongated channels, tubular steel, box beams or I-beams 12 (only one of which is illustrated) extending longitudinally of the table and a number of transversely extending box beams, tube or channel members 14. The longitudinal and transverse members are secured together and are further secured to upright tubular or beam members 16 supported on the floor to form a rigid frame for supporting a platform 18 hereinafter described. The top of the platform 18 preferably is approximately in the order of two to three feet above the floor, and stairs 20 at each end of the frame structure are disposed so that a patient P may easily walk up onto and exit from the platform 18, and a handrail 22 may be utilized as necessary.

The platform 18 is transparent and is preferably formed from an optically clear, rigid abrasion resistant and internally reflective material, such as acrylic plastic or similar material having these properties. It is envisioned that a practical working length of the platform would be approximately 32 feet long so that the patient may make approximately 10 full strides to thereby ensure that the natural gait is obtained. Thus, four sheets of acrylic material, each being an eight foot length and approximately 30 inches wide by one inch thick, is supported on the longitudinal and transverse transport platform support members 12, 14 in lengthwise abutting fashion, preferably with a gasket material such as neoprene (not illustrated) disposed between the platform sheets and the support members.

Figure 3:
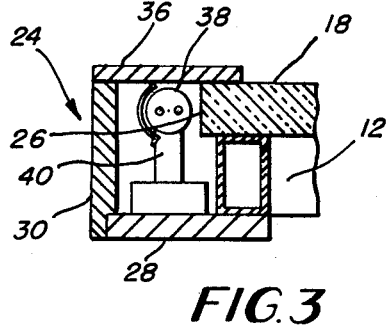
FIG. 3 is a cross sectional view of a portion of the platform taken substantially along line 3—3 of FIG. 1.

An elongated housing 24 is disposed adjacent one edge 26 of the platform 18, that edge preferably being a longitudinally elongated side edge formed by adjacent longitudinal edges of the acrylic sheet. The housing 24, which may be formed in a number of sections such as the platform, as best illustrated in FIG. 3, comprises a bottom plate 28 secured to the frame, a side plate 30 fastened to the bottom plate remote from the platform edge 26, a pair of end plate members 32, 34 secured to the bottom and side plates a their respective longitudinal extremities and a top plate 36 which removeably rests on the upper edge of the side plate 30 and a small portion of the upper surface of the platform adjacent the edge 26. Thus, a small portion of the platform enters the housing 24 and the housing is enclosed except for the side which opens onto the edge 26. Positioned within the housing is lighting means having high intensity light emitted with little heat released, such as a series of florescent lamps 38 supported in lamp fixtures 40 adjacent the edge 26, the distance between the edge 26 and the surface of the lamps being in the order of approximately ¼ of an inch. Disposed about the other edges of the acrylic sheets of the platform is reflective material 42 which may be a reflective tape, mirror, or foil such as an aluminum adhesive tape which reflects the light from the lamps 38 back into the platform to prevent the light from escaping from the edges therefrom, thereby providing a high degree of contrast between the areas of contact and noncontact of the patient's foot when viewed from beneath the platform.

Figure 5:
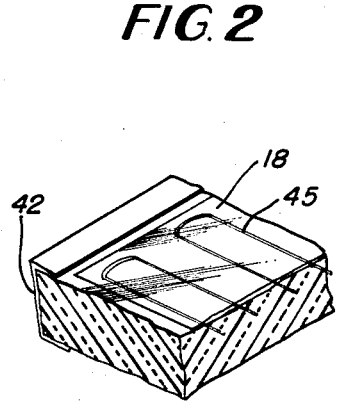
FIG. 5 is a view similar to FIG. 4 but illustrating a modification thereof.
Figure 4:
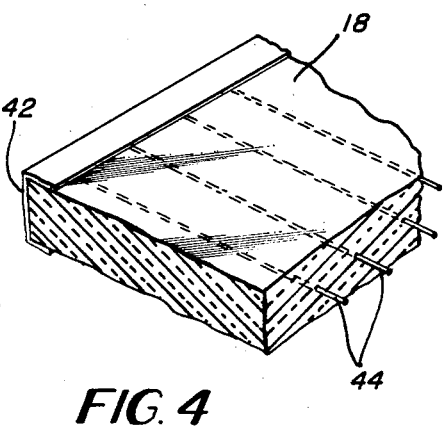
FIG. 4 is a cross sectional view of a portion of the platform taken substantially along line 4—4 of FIG. 1.

To prevent condensation from forming on the surface of the platform due to the temperature difference between the platform surfaces and the patient's foot, the acrylic sheets are heated to approximately 90° F. which is substantially that of normal human body surface temperature. This is accomplished either by embedding electrical heating wires 44 within the acrylic sheets as illustrated in FIG. 4, or by the use of thermal electric heating strips 45 placed on the upper surface of the platform as illustrated in FIG. 5, the wires or strips extending transversely and being equally spaced apart so as to act as a scale for measurement and reference as the patient strides across the platform.

To observe the plantar aspects of the foot and to obtain a record thereof to enable anylsis of the contact and noncontact areas of the foot while in motion, the present invention provides a moving camera 46 for recording the feet from beneath the platform 18 while the patient is striding. Preferably the camera 46 is a video camera and a VCR recorder 48 and monitor 50 may be used to view and monitor the feet while the patient is moving. The camera 46 is mounted on a small trolley or carriage 52 rollable on rails 54 disposed beneath the platform and driven in synchronism with the strides of the patient. To this end a simple cable and pulley drive system may be utilized for coordinating the movement of the trolley with the patient. As illustrated, a belt 56, light harness or similar patient worn, carried or engaged device is secured at the front to a first cable 58 which may pass through an aperture 60 in the stairs or platform frame such as at the upper step at one end of the platform. The cable is trained about a plurality of pulleys 62, 64 and 66 and fastened to the trolley at one end, while another cable 68 is secured to the rear of the belt 56 and passes through an aperture 70 in the other end of the platform and trained about another set of pulleys 72, 74 and 76. Consequently, as the patient P strides along the platform 18, the trolley and thus the camera 46 follows his or her movement below the platform and records the contact and noncontact areas of the foot.

The information obtained as the patient strides along the platform may be viewed on the monitor or recorded on the recorder and may be computer enhanced by means of a computer 78 with an appropriate enhancement and skeleton simulation program. Since the platform permits the patient to take a relatively large number of steps so that his or her natural gait is not altered, the camera will view the true plantar aspects of the patient's feet while in motion permitting the gait cycle to be analyzed in minute detail for diagnostic and corrective purposes.

Numerous alterations of the structure herein disclosed suggest themselves to those skilled in the art. However, it is to be understood that the present disclosure relates to the preferred emodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method of analyzing the gait of a human subject comprising,
    (a) having the subject whose gait is being analyzed make a number of strides along a surface of a transparent platform;
    (b) viewing by means of a camera the plantar aspects of at least one foot of the subject from beneath the platform; and
    (c) moving the camera in response to the strides of the subject so that the plantar aspects of said foot may be monitored while the subject is moving.

2. The method as recited in claim 1, including illuminating an edge of said platform with light while reflecting the light into the platform at other edges of the platform to obtain a high degree of contrast between the contact and noncontact areas of the foot with said surface.

3. The method as recited in claim 1, including heating the platform to preclude the formation of condensation on said surface due to contact of the foot with said surface.

4. The method as recited in claim 3, including illuminating an edge of said platform with light while reflecting the light into the platform at other edges of the platform to obtain a high degree of contrast between the contact and noncontact areas of the foot with said surface.

5. The method as recited in claim 1, wherein the camera movement is synchronized with and follows the subject.

6. Apparatus for use in analyzing the natural gait of a subject while striding comprising, an elongated transparent platform having a surface on which the subject may make a number of strides, a camera, means for mounting said camera for viewing from beneath said platform the plantar aspects of at least one foot of said subject, and drive means for moving said camera in response to the strides of the subject so that the plantar aspects of said foot may be monitored throughout at least one full gait cycle while the subject is moving.

7. Apparatus as recited in claim 6, including means for mounting a light emitting means adjacent an edge of said platform, and reflecting means disposed along other edges of the platform for reflecting the emitted light into the platform.

8. Apparatus as recited in claim 6, including heating means for heating the platform to preclude the formation of condensation on said surface due to contact of the foot with said surface.

9. Apparatus as recited in claim 8, including means for mounting a light emitting means adjacent an edge of said platform, and reflecting means disposed along other edges of the platform for reflecting the emitted light into the platform.

10. Apparatus as recited in claim 6, wherein said drive means comprises a trolley for supporting said camera, a member adapted to be carried by said subject, and means connecting said member to said trolley for moving said trolley in synchronism with the striding of the subject.

11. Apparatus as recited in claim 7, wherein said means for mounting said light emitting means comprises a housing, means for mounting said housing adjacent said edge of said platform, said housing being enclosed about said light emitting means but open between said edge and said light emitting means.

12. Apparatus as recited in claim 8, wherein said heating means comprises electric heating members in contact with said platform.

13. Apparatus as recited in claim 12, including means for mounting a light emitting means adjacent an edge of said platform, and reflecting means disposed along other edges of the platform for reflecting the emitted light into the platform.

14. Apparatus as recited in claim 13, wherein said means for mounting said light emitting means comprises a housing, means for mounting said housing adjacent said edge of said platform, said housing being enclosed about said light emitting means but open between said edge and said light emitting means.

15. Apparatus as recited in claim 10, including means for mounting a light emitting means adjacent an edge of said platform, and reflecting means disposed along other edges of the platform for reflecting the emitted light into the platform.

16. Apparatus as recited in claim 15, including heating means for heating the platform to preclude the formation of condensation on said surface due to contact of the foot with said surface.

17. Apparatus as recited in claim 16, wherein said means for mounting said light emitting means comprises a housing, means for mounting said housing adjacent said edge of said platform, said housing being enclosed about said light emitting means but open between said edge and said light emitting means.

18. Apparatus as recited in claim 17, wherein said heating means comprises electric heating members in contact with said platform.

19. Apparatus as recited in claim 10, including heating means for heating the platform to preclude the formation of condensation on said surface due to contact of the foot with said surface.

20. Apparatus as recited in claim 10, wherein said member comprises a belt, and said means connecting said member to said trolley comprises cable means, a plurality of pulleys, said cable means being trained about said pulleys for synchronously driving said trolley with the striding of said subject.

* * * * *